(12) United States Patent
Rands et al.

(10) Patent No.: US 11,771,681 B2
(45) Date of Patent: *Oct. 3, 2023

(54) THERAPEUTIC COMPOUNDS

(71) Applicant: SMALL PHARMA LTD, London (GB)

(72) Inventors: Peter Rands, London (GB); Zelah Joel, London (GB); Tiffanie Benway, London (GB)

(73) Assignee: SMALL PHARMA LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/890,664

(22) Filed: Jun. 2, 2020

(65) Prior Publication Data

US 2020/0390746 A1    Dec. 17, 2020

(30) Foreign Application Priority Data

Jun. 3, 2019 (GB) .................................. 1907871

(51) Int. Cl.
A61K 31/4045    (2006.01)

(52) U.S. Cl.
CPC ...... *A61K 31/4045* (2013.01); *C07B 2200/05* (2013.01)

(58) Field of Classification Search
CPC ........... A61K 31/4045; A61K 2300/00; A61P 25/30; A61P 25/22; A61P 25/24; A61P 25/18; A61P 25/00; C07D 209/16; C07B 2200/05

See application file for complete search history.

(56) References Cited

U.S. PATENT DOCUMENTS

| | | | |
|---|---|---|---|
| 4,336,378 A | 6/1982 | Sandoz et al. | |
| 8,268,856 B2 | 9/2012 | Hamann et al. | |
| 11,000,534 B1 | 5/2021 | Sippy et al. | |
| 11,242,318 B2 | 2/2022 | Nivorozhkin et al. | |
| 2002/0022667 A1 | 2/2002 | Pace et al. | |
| 2009/0076121 A1 | 3/2009 | Czanik et al. | |
| 2018/0221396 A1 | 8/2018 | Chadeayne et al. | |
| 2020/0339519 A1 | 10/2020 | Kim et al. | |
| 2020/0397752 A1* | 12/2020 | Perez Castillo | A61K 45/06 |
| 2021/0378969 A1 | 12/2021 | Rands et al. | |
| 2021/0395201 A1 | 12/2021 | Rands et al. | |
| 2021/0403426 A1 | 12/2021 | Rands et al. | |
| 2022/0062237 A1 | 3/2022 | Layzell et al. | |
| 2022/0062238 A1 | 3/2022 | Layzell et al. | |
| 2022/0081396 A1 | 3/2022 | Rands et al. | |
| 2022/0168275 A1 | 6/2022 | Rands et al. | |

FOREIGN PATENT DOCUMENTS

| | | |
|---|---|---|
| GB | 2585978 A | 1/2021 |
| GB | 2586940 A | 3/2021 |
| GB | 2596884 A | 1/2022 |
| WO | WO 02083144 A1 | 10/2002 |
| WO | WO 2004-085392 A | 10/2004 |
| WO | WO 2008-049116 A1 | 4/2008 |
| WO | WO 2008-071455 A1 | 6/2008 |
| WO | WO 2009-049030 A | 4/2009 |
| WO | WO 2018-195455 A1 | 10/2018 |
| WO | 2019-081764 A1 | 5/2019 |
| WO | WO 2020-169850 A | 8/2020 |
| WO | WO 2020-169851 A1 | 8/2020 |
| WO | WO 2020-176597 A1 | 9/2020 |
| WO | WO 2020-176599 A1 | 9/2020 |
| WO | WO 2020-245133 A1 | 12/2020 |
| WO | WO 2021089872 A1 | 5/2021 |
| WO | WO 2021089873 A1 | 5/2021 |
| WO | WO 2021-116503 A1 | 6/2021 |
| WO | WO 2021-155470 A1 | 8/2021 |
| WO | WO 2021-234608 A1 | 11/2021 |
| WO | 2022031566 A1 | 2/2022 |

(Continued)

OTHER PUBLICATIONS

Barker (Front. Neurosci. (2018) 12:536, 17 pages).*
Beaton et al. (Pharmacology Biochemistry & Behavior, vol. 16, pp. 811-814, 1982).*
Morris et al. (J Label Compd Radiopharm, (1993) 33: 455-465).*
Dyck et al. (Biochemical Pharmacology, vol. 35, No. 17. pp. 2893-2896, 1986).*
Brandt et al. (J. Label. Compd. Radiopharm. (2008) 51, p. 423-429).*
Kazakevich et al. ("HPLC for Pharmaceutical Scientists", publ May 18, 2006, Wiley, 1118 pages).*
Strassman et al. (Arch Gen Psychiatry. 1994;51(2):85-97).*
Atzrodt et al. (Angew. Chem. Int. Ed. 2018, 57, 1758-1784).*

(Continued)

*Primary Examiner* — Robert H Havlin

(74) *Attorney, Agent, or Firm* — Heslin Rothenberg Farley & Mesiti P.C.

(57) ABSTRACT

The present invention relates to compositions comprising N,N-dimethyltryptamine, deuterated N,N-dimethyltryptamine and/or partially deuterated N,N-dimethyltryptamine. In particular, the present invention relates to compositions comprising a combination of N,N-dimethyltryptamine and 2% or more by weight of one or more deuterated N,N-dimethyltryptamine compound selected from α,α-dideutero-N,N-dimethyltryptamine and α,α,β,β-tetradeutero-N,N-dimethyltryptamine. Additional and alternative compositions of the present invention comprise a combination of N,N-dimethyltryptamine and 2% or more by weight of one or more partially deuterated N,N-dimethyltryptamine compound selected from α,β,β-trideutero-N,N-dimethyltryptamine, α,β-dideutero-N,N-dimethyltryptamine, and α-deutero-N,N-dimethyltryptamine. Methods of synthesising compositions of the present invention, and methods of use of presently described compositions in treating psychiatric or psychocognitive disorders, such as major depressive disorder, are also provided.

9 Claims, 2 Drawing Sheets

(56) References Cited

FOREIGN PATENT DOCUMENTS

| WO | 2022043227 A1 | 3/2022 |
| WO | 2022069690 A2 | 4/2022 |

OTHER PUBLICATIONS

Brandt, et al., "Microwave-accelerated synthesis of psychoactive deuterated N,N-dialkylated- [ [alpha=, [alpha], [beta], [beta] -d 4]—tryptamines", Nov. 1, 2008, 7 pages.

Walker, et al., "Gas Chromatographic-Mass Spectrometric Isotope Dilution Assay for N,N-Dimethyltryptamine in Human Plasma", Aug. 1972, 9 pages.

Celik, et al., "Binding of Serotonin to the Human Serotonin Transporter. Molecular Modeling and Experimental Validation", Journal of the American Chemical Society, Mar. 2008, 13 pages.

Celik, et al., "Supplementary information to Binding of Serotonin to the Human Serotonin Transporter. Molecular Modeling and Experimental Validation", Journal of the American Chemical Society, Mar. 2008, 14 pages.

Halberstadt, et al., "Behavioral effects of tetradeutero in rats: comparison with 5-MeO-DMT administered in combination with a monoamine oxidase inhibitor", Jan. 2012, 10 pages.

Tearavarich, Microwave-accelerated preparation and analytical characterization of 5-ethoxy-N,N-dialkyl-and-tryptamines, Dec. 2010, 13 pages.

Beaton, "A Comparison of the Behavioral Effects of Proteo-And Deutero-N, N-Dimethyltryptamine", Alabama, Sep. 8, 1981, 5 pages.

Baker, "Comparison of the Brain Levels of N,N-Dimethyltryptamine and A-,A-,/3,/3-Tetradeutero- N,N-Dimethyltryptamine Following Intraperitoneal Injection", Alabama, Oct. 1981, 5 pages.

Morris, "Indolealkylamine Metabolism:Synthesis of Deuterated Indolealkylamines as Metabolic Probes", Alabama, Oct. 8, 1992, 12 pages.

Ambinter Screening Library, Publication Date Mar. 26, 2020, Order No. Cat. Amb33838664.

Aurora Building Blocks 2, Publication Date Feb. 27, 2020, Order No. Cat A17.921.638.

MuseChem Product List, Publication Date Apr. 21, 2020, Order No. Cat. R055190.

Cameron, et el., "Effects of N,N-Dimethyltryptamine on Rat Behaviors Relevant to Anxiety and Depression", ACS Chemical Neuroscience, 2018, 18 pages.

Chemieliva Pharmaceutical Product List, Order No. Cat. CC0034141.
Chemieliva Pharmaceutical Product List, Order No. Cat. CC0034145.
Dunlap, et al., "Identification of Psychoplastogenic N,N-Dimethylaminoisotryptamine (isoDMT) Analogues through Structure—Activity Relationship Studies", Journal of Medicinal Chemistry, 2020, 14 pages.

Gaujac, et al., Investigations into the polymorphic properties of N,N-dimethyltryptamine by X-ray diffraction and differential scanning calorimetry, Microchemical Journal, 2013, 26 pages.

Ghosal, et al., "Indole Bases of Desmodium Gyrans" Phytochemistry (Elsevier), vol. 11, No. 5, 1972, 2 pages.

Grina, et al., "Old and New Alkaloids from Zanthoxylum arborescens", Journal of Organic Chemistry, vol. 47, No. 13, Dec. 18, 1981, 4 pages.

Ibrahim, et al., "Marine inspired 2-(5-Halo-1H-indol-3-yl)-N,N-dimethylethanamines as Modulators of Serotonin Receptors: An Example Illustrating the Power of Bromine as Part of the Uniquely Marine Chemical Space", Marine drugs, 2017, 14 pages.

Mlcilhenny, et al., "Direct analysis of psychoactive tryptamine and harmala alkaloids in the Amazonian botanical medicine ayahuasca by liquid", Journal of Chromatography A, vol. 1216, No. 51, 9 pages.

Queiroz, et al., "Chemical Composition of the Bark of Tetrapterys Mucronate and Identification of Acetrylcholinesterase Inhibitory Constituents" Journal of Natural Products, vol. 77, No. 3, 2014, 7 pages.

Riga, et al., The serotonin hallucinogen 5-MeO-DMT alters corticothalamic activity in freely moving mice: Regionally-selective involvement of 5-HT1A and 5-HT2A receptors, Neuropharmacology, 2017, 12 pages.

Sard, et al., "SAR of psilocybin analogs: Discovery of a selective 5-HT2c agonist", Bioorganic & Medicinal Chemistry Letters 15, 2005, 5 pages.

Servillo, et al., "Citrus Genus Plants Contain N-Methylated Tryptamine Derivatives and Their 5-Hydroxylated Forms", Journal of Agricultural and Food Chemistry, 2013, 7 pages.

Strassman, et al., "Dose-Response Study of N, N-Dimethyltryptamine in Humans: II. Subjective Effects and Preliminary Results of a New Rating Scale", Archives of General Psychiatry, Chicago, IL, Feb. 1994, 18 pages.

Timmins, et al. "Deuterated drugs; where are we now?" Expert Opin ther Pat., Oct. 2014, 19 pages.

Rands et al., Unpublished U.S. Appl. No. 17/616,345, filed Dec. 3, 2021.

Rands et al., Unpublished U.S. Appl. No. 17/469,063, filed Sep. 8, 2021.

Rands et al., Unpublished U.S. Appl. No. 17/574,424, filed Jan. 12, 2022.

Rands et al., Unpublished U.S. Appl. No. 17/680,411, filed Feb. 25, 2022.

Brito-Da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.

Roseman et al., "Quality of Acute Psychedelic Experience Predicts Therapeutic Efficacy of Psilocybin for Treatment—Resistant Depression", Frontiers in Pharmacology, vol. 8, Article 974, 10 pages. Jan. 2018.

Reiff et al., "Psychedelics and Psychedelic-Assisted Psychotherapy", Am J. Psychiatry, 177:5, pp. 391-410. May 2020.

U.S. Appl. No. 18/252,949 to Rands et al. filed May 15, 2023.

* cited by examiner

THERAPEUTIC COMPOUNDS

CROSS-REFERENCE TO RELATED APPLICATIONS

This application claims priority from United Kingdom Application No. 1907871.6, filed Jun. 3, 2019, the disclosure of which is incorporated by reference herein in its entirety.

FIELD OF THE INVENTION

The present invention relates to compositions comprising two or more compounds selected from N,N-dimethyltryptamine, deuterated N,N-dimethyltryptamine, and partially deuterated N,N-dimethyltryptamine.

In particular, the present invention relates to compositions comprising a combination of N,N-dimethyltryptamine and 2% or more by weight of one or more deuterated N,N-dimethyltryptamine compounds selected from $\alpha,\alpha$-dideutero-N,N-dimethyltryptamine and $\alpha,\alpha,\beta,\beta$-tetradeutero-N,N-dimethyltryptamine. Additional and alternative compositions of the present invention comprise a combination of N,N-dimethyltryptamine and 2% or more by weight of one or more partially deuterated N,N-dimethyltryptamine compounds selected from $\alpha,\beta,\beta$-trideutero-N,N-dimethyltryptamine, $\alpha,\beta$-dideutero-N,N-dimethyltryptamine, and $\alpha$-deutero-N,N-dimethyltryptamine. Methods of synthesizing compositions of the present invention, and methods of use of such compositions in treating psychiatric or psychocognitive disorders, such as major depressive disorder, are also provided.

BACKGROUND OF THE INVENTION

Classical psychedelics have shown preclinical and clinical promise in treating psychiatric disorders (Carhart-Harris and Goodwin (2017), *The Therapeutic Potential of Psychedelic Drugs: Past, Present and Future*, Neuropsychopharmacology 42, 2105-2113). In particular, psilocybin has demonstrated significant improvement in a range of depression and anxiety rating scales in randomised double blind studies (Griffiths et al. (2016), *Psilocybin produces substantial and sustained decreases in depression and anxiety in patients with life-threatening cancer: a randomised double-blind trial*, Journal of Psychopharmacology 30(12), 1181-1197).

N,N-dimethyltryptamine (DMT) is also understood to hold therapeutic value as a short-acting psychedelic, however its duration of action (under 20 minutes) is so short as to limit effective therapy. Administration protocols have been developed to extend the immersive psychedelic experience of DMT (Gallimore and Strassman (2016), *A model for the application of target-controlled intravenous infusion for a prolonged immersive DMT psychedelic experience*, Frontiers in Pharmacology, 7:211). However, these protocols carry risk of toxic buildup in patients who are poor metabolisers of DMT (for further discussion see Strassman et al (1994), *Dose response study of N,N-dimethyltryptamine in humans*, Arch Gen Psychiatry 51, 85).

$\alpha,\alpha,\beta,\beta$-Tetradeutero-N,N-dimethyltryptamine is known to exhibit a kinetic isotope effect which bestows a significant difference on its in vivo pharmacokinetic profile as compared with N,N-dimethyltryptamine. Substitution of hydrogen with a deuterium at an spa carbon centre is known to give rise to a 'kinetic isotope effect' by virtue of the difference in bond strength between a CH and a CD bond. First demonstrated in 1982 (Barker et al. (1982), *Comparison of the brain levels of N,N-dimethyltryptamine and $\alpha,\alpha,\beta,\beta$-tetradeutero-N,N-dimethyltryptamine following intraperitoneal injection*, Biochemical Pharmacology, 31(15), 2513-2516), the halflife of $\alpha,\alpha,\beta,\beta$-tetradeutero-N,N-dimethyltryptamine in the rodent brain is suggestive that administration of $\alpha,\alpha,\beta,\beta$-tetradeutero-N,N-dimethyltryptamine alone would maintain a patient in DMT space for longer than therapeutically essential.

SUMMARY OF THE INVENTION

The present invention is based, in part, upon the ability to apply knowledge of the kinetic isotope effect exhibited by $\alpha,\alpha,\beta,\beta$-tetradeutero-N,N-dimethyltryptamine in order to modify, controllably, the pharmacokinetic profile of N,N-dimethyltryptamine, thereby permitting more flexible therapeutic application. In particular, by providing individual drug substance compositions comprising mixtures of N,N-dimethyltryptamine and deuterated N,N-dimethyltryptamine analogues, in particular N,N-dimethyltryptamine comprising at least one deuterium atom at the alpha position (i.e. attached to the carbon atom to which the dimethylamino moiety is attached) and, according to certain embodiments, one or two deuterium atoms at the beta position, the present invention provides compositions and methods which enable a finely tuned single dose to maintain a patient in full dissociation from the external world, referred to herein as 'DMT space', for a therapeutically optimised duration without relying on infusion protocols or combination therapy with monoamine oxidase inhibitors in the clinic. The present invention provides a clinically applicable solution which reduces clinical complexity and increases clinical flexibility in the administration of DMT-assisted psychotherapy.

Moreover, we have observed a quantifiable relationship between the extent of deuteration, and by proxy the H:D ratio of input reducing agent in synthetic methods disclosed herein, and the effect on potentiation of the metabolic half-life of the parent compound. Such technical effect may be used to quantifiably increase the precision with which compositions comprising pluralities of N,N-dimethyltryptamine compounds (that is to say comprising more than one type of compound selected from N,N-dimethyltryptamine and its deuterated analogues, in particular those deuterated at the alpha and optionally beta positions, or pharmaceutically acceptable salts of these) may be prepared.

Viewed from a first aspect, therefore, the invention provides a composition comprising two or more compounds selected from N,N-dimethyltryptamine, $\alpha,\alpha$-dideutero-N,N-dimethyltryptamine compounds, $\alpha$-protio,$\alpha$-deutero-N,N-dimethyltryptamine compounds and pharmaceutically acceptable salts of these compounds.

Viewed from a second aspect, the invention provides a composition obtainable by the reduction of 2-(3-indolyl)-N,N-dimethylglyoxalamide with a reducing agent consisting essentially of up to 90 mol % of lithium aluminium hydride and 10 mol % or more of lithium aluminium deuteride.

Viewed from a third aspect, the invention provides a composition obtainable by the reduction of 2-(3-indolyl)-N,N-dimethylacetamide with a reducing agent consisting essentially of up to 90 mol % by weight of lithium aluminium hydride and 10 mol % or more of lithium aluminium deuteride.

Viewed from a fourth aspect, the invention provides a pharmaceutical composition comprising a composition as defined according to any one of the first to third aspects in combination with a pharmaceutically acceptable excipient.

Viewed from a fifth aspect, the invention provides a composition as defined according to any one of the first to fourth aspects for use in therapy.

Viewed from a sixth aspect, the invention provides a composition as defined according to any one of the first to fourth aspects for use in a method of treating a psychocognitive disorder in a patient.

Viewed from a seventh aspect, the invention provides a method of treating a psychocognitive disorder comprising administering to a patient in need thereof a composition as defined according to any one of the first to fourth aspects.

Viewed from a eighth aspect, the invention provides the use of a composition as defined according to any one of the first to fourth aspects in the manufacture of a medicament for use in a method of treating a psychocognitive disorder in a patient.

Viewed from a ninth aspect, the invention provides a method of preparing a composition in accordance with any of the first to third aspects of the invention comprising contacting 2-(3-indolyl)-N,N-dimethylglyoxalamide and/or 2-(3-indolyl)-N,N-dimethylacetamide with a reducing agent consisting essentially of up to 90 mol % of lithium aluminium hydride and 10 mol % or more of lithium aluminium deuteride.

Viewed from an tenth aspect, the invention provides a compound selected from $\alpha,\beta,\beta$-trideutero-N,N-dimethyltryptamine, $\alpha,\alpha,\beta$-trideutero-N,N-dimethyltryptamine, $\alpha,\beta$-dideutero-N,N-dimethyltryptamine, and $\alpha$-deutero-N,N-dimethyltryptamine.

Further aspects and embodiments of the present invention will be evident from the discussion that follows below.

DETAILED DESCRIPTION OF THE INVENTION

Figure 1:
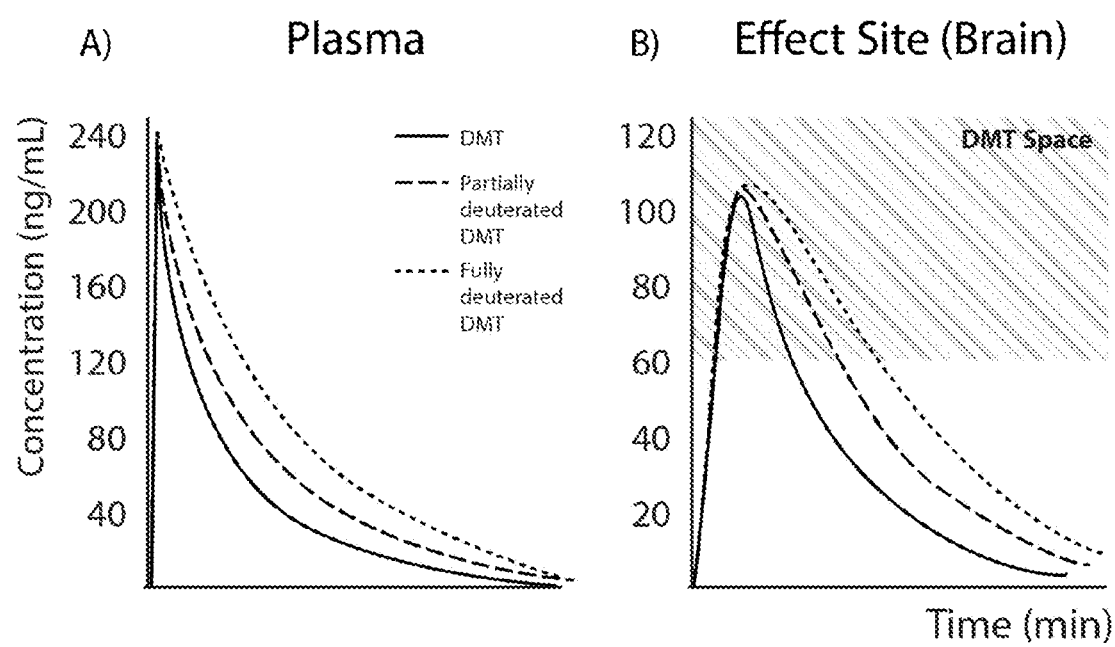
FIG. 1. depicts the predicted pharmacokinetic profile of partially deuterated DMT compared to DMT and fully deuterated DMT. Predicted A) plasma concentration and B) brain tissue concentration, showing the extended half-life of partially deuterated DMT. Hashed area depicts effect site concentrations (>60 ng/mL) that are experienced as full dissociation from the external world, referred to as 'DMT space'.

Throughout this specification, one or more aspect of the invention may be combined with one or more features described in the specification to define distinct embodiments of the invention.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention provides a composition comprising two or more compounds selected from N,N-dimethyltryptamine, $\alpha,\alpha$-dideutero-N,N-dimethyltryptamine compounds, $\alpha$-protio, $\alpha$-deutero-N,N-dimethyltryptamine compounds and pharmaceutically acceptable salts of these compounds.

A deuterium atom is a hydrogen atom with an additional neutron.

Frequently herein, the terms $\alpha,\alpha$-dideutero-N,N-dimethyltryptamine compounds and $\alpha$-protio, $\alpha$-deutero-N,N-dimethyltryptamine compounds are referred to as deuterated (or fully deuterated) N,N-dimethyltryptamine and partially deuterated N,N-dimethyltryptamine respectively. A deuterated (or fully deuterated) N,N-dimethyltryptamine thus refers strictly to an N,N-dimethyltryptamine compound with both protons at the $\alpha$ position substituted with deuterium atoms. The term partially deuterated N,N-dimethyltryptarnine strictly refers to an N,N-dimethyltryptamine compound in which one of the two protons at the $\alpha$ position is substituted with a deuterium atom. A deuterated N,N-dimethyltryptamine compound of the present invention is any N,N-dimethyltryptamine compound substituted with two deuterium atoms at the $\alpha$ position, and a partially deuterated N,N-dimethyltryptamine compound of the present invention is any N,N-dimethyltryptamine compound with one hydrogen atom and one deuterium atom at the $\alpha$ position.

Accordingly, the invention provides a composition comprising two or more compounds selected from N,N-dimethyltryptamine, deuterated N,N-dimethyltryptamine, and partially deuterated N,N-dimethyltryptamine, that is a composition comprising a combination of N-dimethyltryptamine and one or more deuterated or partially deuterated N,N-dimethyltryptamine compounds.

N,N-dimethyltryptamine and all its deuterated analogues freely form addition salts with anionic counterions. Throughout the specification, an N,N-dimethyltryptamine compound (in particular N,N-dimethyltryptamine, $\alpha,\alpha$-dideutero-N,N-dimethyltryptamine compounds and $\alpha$-protio, $\alpha$-deutero-N,N-dimethyltryptamine compounds) refers equally to any pharmaceutically acceptable salt, e.g. the fumarate salt.

Typically, acidic reagents may be used to prepare salts, in particular pharmaceutically acceptable salts, of N,N-dimethyltryptamine compounds. Examples of suitable acidic reagents are selected from the group consisting of fumaric acid, hydrochloric acid, tartaric acid, citric acid, hydrobromic acid, sulfuric acid, phosphoric acid, acetic acid, maleic acid, lactic acid, tartaric acid and gluconic acid. Often, where in the form of salts, N,N-dimethyltryptamine compounds, in particular as the compounds of the invention, in the compositions of the invention or otherwise used according to the various aspects of the present invention, and embodiments thereof, are fumarate, hydrochloride, tartrate or citrate salts, in particular fumarate salts.

The compounds present in the composition of the first aspect of the invention, and indeed those of the second and third (and other, as appropriate) aspects of the invention, may thus be present as N,N-dimethyltryptamine compounds, in particular N,N-dimethyltryptamine or deuterated or partially deuterated N,N-dimethyltryptamine compounds as defined herein, in free base or salt form (such as the salts described herein), optionally as solvates (e.g. hydrates) thereof.

According to particular embodiments of the invention, α,α-dideutero-N,N-dimethyltryptamine compounds (fully deuterated compounds) comprise 0, 1 or 2 deuterium atoms at the β position but, other than the presence of 2, 3 or 4 deuterium atoms, are identical to the compound N,N-dimethyltryptamine. According to these particular and other particular embodiments of the invention, α-protio, α-deutero-N,N-dimethyltryptamine compounds (partially deuterated compounds) may also comprise 0, 1 or 2 deuterium atoms at the β position but, other than the presence of 1, 2 or 3 deuterium atoms, are identical to the compound N,N-dimethyltryptamine. The six fully deuterated and partially deuterated compounds according to these particular embodiments of the invention are depicted in the following table:

Deuterated N,N-dimethyltryptamine compounds

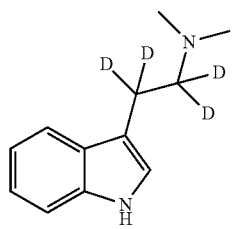 [SMILES: [2H]C([2H])(c1c[nH]c2ccccc12)C([2H])([2H])N(C)C]

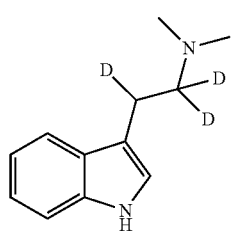 [SMILES: [2H]C(c1c[nH]c2ccccc12)C([2H])([2H])N(C)C]

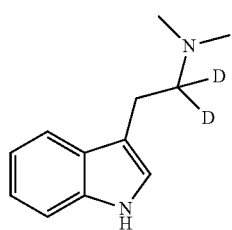 [SMILES: [2H]C([2H])(Cc1c[nH]c2ccccc12)N(C)C]

Partially deuterated N,N-dimethyltryptamine compounds

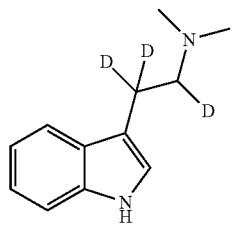 [SMILES: [2H]C(N(C)C)C([2H])([2H])c1c[nH]c2ccccc12]

-continued

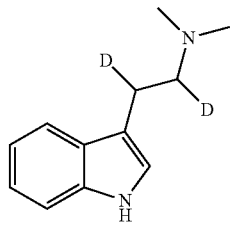 [SMILES: [2H]C(c1c[nH]c2ccccc12)C([2H])N(C)C]

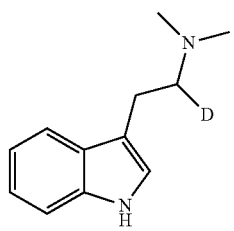

In preferred embodiments of the first aspect, the composition comprises 2% or more by weight of the one or more deuterated or partially deuterated N,N-dimethyltryptamine compounds. In preferred embodiments of the first aspect, the composition comprises 5% or more by weight of the one or more deuterated or partially deuterated N,N-dimethyltryptamine compounds. In preferred embodiments of the first aspect, the composition comprises 10% or more by weight of the one or more deuterated or partially deuterated N,N-dimethyltryptamine compounds. In preferred embodiments of the first aspect, the composition comprises 15% or more by weight of the one or more deuterated or partially deuterated N,N-dimethyltryptamine compounds. In preferred embodiments of the first aspect, the composition comprises 20% or more by weight of the one or more deuterated or partially deuterated N,N-dimethyltryptamine compounds. In preferred embodiments of the first aspect, the composition comprises 25% or more by weight of the one or more deuterated or partially deuterated N,N-dimethyltryptamine compounds. In preferred embodiments of the first aspect, the composition comprises 30% or more by weight of the one or more deuterated or partially deuterated N,N-dimethyltryptamine compounds. In preferred embodiments of the first aspect, the composition comprises 50% or more by weight of the one or more deuterated or partially deuterated N,N-dimethyltryptamine compounds. In preferred embodiments of the first aspect, the composition comprises 60% or more by weight of the one or more deuterated or partially deuterated N,N-dimethyltryptamine compounds. In preferred embodiments of the first aspect, the composition comprises 75% or more by weight of the one or more deuterated or partially deuterated N,N-dimethyltryptamine compounds. In preferred embodiments of the first aspect, the composition comprises up to 90% by weight of the one or more deuterated or partially deuterated N,N-dimethyltryptamine compounds. In preferred embodiments of the first aspect, the composition comprises up to 95% by weight of the one or more deuterated or partially deuterated N,N-dimethyltryptamine compounds. In preferred embodiments of the first aspect, the composition comprises up to 96% by weight of the one or more deuterated or partially deuterated N,N-dimethyltryptamine compounds. In preferred embodiments of the first aspect, the composition comprises up to 97% by weight of the one or more deuterated or partially deuterated N,N-dimethyltryptamine compounds. In preferred embodiments of the first aspect, the composition comprises up to 98% by weight of the one or more deuterated or partially deuterated N,N-dimethyltryptamine compounds.

Accordingly, it will be understood from the foregoing that, according to particular embodiments of the first aspect of the invention, in particular those embodiments discussed in the following eight paragraphs, the composition comprises between 2% and 90%, 2% and 95%, 2% and 96%, 2% and 97%, 2% and 98%, for example between 5% and 90%, 5% and 95%, 5% and 96%, 5% and 97%, 5% and 98%; 10% and 90%, 10% and 95%, 10% and 96%, 10% and 97%, 10% and 98%; 15% and 90%, 15% and 95%, 15% and 96%, 15% and 97%, 15% and 98%; 20% and 90%, 20% and 95%, 20% and 96%, 20% and 97%, 20% and 98%; 25% and 90%, 25% and 95%, 25% and 96%, 25% and 97%, 25% and 98%; 30% and 90%, 30% and 95%, 30% and 96%, 30% and 97%, 30% and 98%; 50% and 90%, 50% and 95%, 50% and 96%, 50% and 97%, 50% and 98%; 60% and 90%, 60% and 95%, 60% and 96%, 60% and 97%, 60% and 98%; or 75% and 90%, 75% and 95%, 75% and 96%, 75% and 97%, 75% and 98%, by weight of the one or more deuterated or partially deuterated N,N-dimethyltryptamine compounds.

In embodiments of the first aspect, the composition comprises a combination of N,N-dimethyltryptamine and one or more deuterated N,N-dimethyltryptamine compounds selected from $\alpha,\alpha$-dideutero-N,N-dimethyltryptamine, $\alpha,\alpha,\beta$-trideutero-N,N-dimethyltryptamine and $\alpha,\alpha,\beta,\beta$-tetradeutero-N,N-dimethyltryptamine, for example a combination of N,N-dimethyltryptamine and $\alpha,\alpha$-dideutero-N,N-dimethyltryptamine, a combination of N,N-dimethyltryptamine and $\alpha,\alpha,\beta,\beta$-tetradeutero-N,N-dimethyltryptamine or a combination of N,N-dimethyltryptamine, $\alpha,\alpha$-dideutero-N,N-dimethyltryptamine and $\alpha,\alpha$-dideutero-N,N-dimethyltryptamine.

In preferred embodiments of the first aspect, the composition comprises a combination of N,N-dimethyltryptamine and 2% or more by weight of one or more deuterated N,N-dimethyltryptamine compounds selected from $\alpha,\alpha$-dideutero-N,N-dimethyltryptamine and $\alpha,\alpha,\beta,\beta$-tetradeutero-N,N-dimethyltryptamine.

In other embodiments of the first aspect, the composition comprises a combination of N,N-dimethyltryptamine and 2% or more by weight of one or more deuterated N,N-dimethyltryptamine compounds selected from $\alpha,\alpha$-dideutero-N,N-dimethyltryptamine, $\alpha,\alpha,\beta$-trideutero-N,N-dimethyltryptamine and $\alpha,\alpha,\beta,\beta$-tetradeutero-N,N-dimethyltryptamine.

In preferred embodiments of the first aspect, the composition comprises 2% or more by weight of $\alpha,\alpha,\beta,\beta$-tetradeutero-N,N-dimethyltryptamine.

In preferred embodiments of the first aspect, the composition comprises 2% or more by weight of $\alpha,\alpha$-dideutero-N,N-dimethyltryptamine.

In certain embodiments of the first aspect, the composition comprises 2% or more by weight of $\alpha,\alpha,\beta,\beta$-tetradeutero-N,N-dimethyltryptamine and 2% or more by weight of $\alpha,\alpha$-dideutero-N,N-dimethyltryptamine.

It will be understood that, wherever a composition comprises 2% or more by weight of one or more deuterated N,N-dimethyltryptamine compounds, that such compositions may comprise up to 95% by weight of one or more deuterated N,N-dimethyltryptamine compounds, or up to 96% by weight, up to 97% by weight or up to 98% by weight.

In preferred embodiments of the first aspect, the composition comprises or further comprises, for example further comprises, one or more partially deuterated N,N-dimethyltryptamine compounds selected from $\alpha,\beta,\beta$-trideutero-N,N-dimethyltryptamine, $\alpha,\beta$-dideutero-N,N-dimethyltryptamine, and $\alpha$-deutero-N,N-dimethyltryptamine. Preferably, the partially deuterated N,N-dimethyltryptamine compound is $\alpha$-deutero-N,N-dimethyltryptamine.

In preferred embodiments, the one or more partially deuterated N,N-dimethyltryptamine compound comprises up to 50% by weight of the total composition.

According to other preferred embodiments of the first aspect of the invention, the composition comprises up to 50% by weight, based on the total weight of the composition, of one or more compounds selected from $\alpha,\alpha$-dideutero-N,N-dimethyltryptamine compounds, $\alpha$-protio, $\alpha$-deutero-N,N-dimethyltryptamine compounds and pharmaceutically acceptable salts thereof. It will be understood that, in such embodiments, such compositions may comprise 2% or more by weight, for example 5% or more, 10% more, 15% more, 20% or more, 25% or more or 30% or more, based on the total composition, of the said one or more compounds.

Typically, the compositions of the invention comprise N,N-dimethyltryptamine.

According to specific embodiments, the compositions of the present invention, including all of the embodiments described herein, including but not limited to those embodiments comprising N,N-dimethyltryptamine, consist essentially of two or more N,N-dimethyltryptamine compounds (i.e. compounds selected from N,N-dimethyltryptamine and its deuterated analogues, in particular those deuterated at the alpha and optionally beta positions, or pharmaceutically acceptable salts of these). By the composition consisting essentially of two or more N,N-dimethyltryptamine compounds is meant that the composition may comprise additional components (other than N,N-dimethyltryptamine compounds) but that the presence of these additional components will not materially affect the essential characteristics of the composition. In particular, compositions consisting essentially of N,N-dimethyltryptamine compounds will not comprise material amounts of other pharmaceutically active substances (i.e. material amounts of other drug substances).

Even more typically, the compositions of the present invention, including all of the embodiments described herein, including but not limited to those embodiments comprising N,N-dimethyltryptamine consist of two or more N,N-dimethyltryptamine compounds.

The composition of the present invention may comprise from 2% to 98% by weight of N,N-dimethyltryptamine, and preferably comprises from 5% to 95% by weight of N,N-dimethyltryptamine. Preferred compositions of the present invention comprise from 10% to 90% by weight of N,N-dimethyltryptamine, or from 15% to 85% by weight of N,N-dimethyltryptamine, or from 20% to 80% by weight of N,N-dimethyltryptamine, or from 25% to 75% by weight of N,N-dimethyltryptamine, or from 30% to 70% by weight of N,N-dimethyltryptamine, or from 40% to 60% by weight of N,N-dimethyltryptamine.

The composition of the present invention preferably comprise from 5% to 95% by weight of a deuterated N,N-dimethyltryptamine compound selected from $\alpha,\alpha$-dideutero-N,N-dimethyltryptamine and $\alpha,\alpha,\beta,\beta$-tetradeutero-N,N-dimethyltryptamine.

The second aspect of the invention provides a composition obtainable by the reduction of 2-(3-indolyl)-N,N-dimethylglyoxalamide with a reducing agent consisting essentially of up to 90 mol % of lithium aluminium hydride and 10 mol % or more of lithium aluminium deuteride; and the third aspect provides a composition obtainable by the reduction of 2-(3-indolyl)-N,N-dimethylacetamide with a reducing agent consisting essentially of up to 90 mol % of lithium aluminium hydride and 10 mol % or more of lithium aluminium deuteride. In both aspects, the reducing agent may be dissolved or suspended in a liquid medium. Typically, owing to strong reactivity with water and protect solvents such as alcohols, although available in solid (powdered) form, lithium aluminium hydride (or deuteride) are often manipulated in dried, aprotic solvents such as ethers, often under an inert atmosphere. The skilled person is well aware of such precautions and appropriate protocols.

It will be understood that the invention thus provides a composition obtainable by the reduction of a composition comprising one or more of 2-(3-indolyl)-N,N-dimethylglyoxalamide and of 2-(3-indolyl)-N,N-dimethylacetamide with a reducing agent consisting essentially of up to 90 molar % of lithium aluminium hydride and 10 molar % or more of lithium aluminium deuteride, optionally dissolved or suspended in a liquid medium. The invention also provides a composition obtained by such reduction or, more generally, obtained by a reduction in accordance with the second or third aspect of the invention.

It is also to be understood that the amounts of N,N-dimethyltryptamine compounds described herein with specific reference to the composition of the first aspect of the invention may be applied mutatis mutandis to the compositions of the second and third aspects of the invention.

Preferably, the reducing agent described herein, e.g. according to the second, third and ninth aspects of the present invention, but also as described in the immediately preceding paragraph, consists essentially of 85 molar % lithium aluminium hydride and 15 molar % lithium aluminium deuteride, or consists essentially of 80 molar % lithium aluminium hydride and 20 molar % of lithium aluminium deuteride, or consists essentially of 25 molar % lithium aluminium hydride and 75 molar % lithium aluminium deuteride, or consists essentially of 30 molar % lithium aluminium hydride and 70 molar % lithium aluminium deuteride, or consists essentially of 65 molar % lithium aluminium hydride and 35 molar % lithium aluminium deuteride, or consists essentially of 60 molar % lithium aluminium hydride and 40 molar % lithium aluminium deuteride, or consists essentially of 55 molar % lithium aluminium hydride and 45 molar % lithium aluminium deuteride, or consists essentially of 50 molar % lithium aluminium hydride and 50 molar % lithium aluminium deuteride, or consists essentially of 45 molar % lithium aluminium hydride and 55 molar % of lithium aluminium deuteride, or consists essentially of 40 molar % by weight of lithium aluminium hydride and 60 molar % of lithium aluminium deuteride, or consists essentially of 35 molar % of lithium aluminium hydride and 65 molar % lithium aluminium deuteride, or consists essentially of 30 molar % lithium aluminium hydride and 70 molar % lithium aluminium deuteride, or consists essentially of 25 molar % lithium aluminium hydride and 75 molar % lithium aluminium deuteride, or consists essentially of 20 molar % lithium aluminium hydride and 80 molar % lithium aluminium deuteride, or consists essentially of 15 molar % by weight of lithium aluminium.

According to particular embodiments, by reciting that the reducing agent consists essentially of lithium aluminium hydride and lithium aluminium deuteride is meant that the reducing agent may comprise additional components but that the presence of these components will not materially affect the essential characteristics of the reducing agent (in particular stability and reductive propensity).

According to the fourth aspect of the invention, there is provided a pharmaceutical composition comprising a composition as defined in accordance with the first to third aspects of the invention, in combination with a pharmaceutically acceptable excipient.

The pharmaceutical composition of the invention comprises a composition of the invention (according to any one of its first to third aspects) in combination with one or more pharmaceutically acceptable excipients. Suitable pharmaceutical compositions can be prepared by the skilled person, with examples of pharmaceutically acceptable excipients including but not being limited to those described in Gennaro et. al., *Remmington: The Science and Practice of Pharmacy*, $20^{th}$ Edition, Lippincott, Williams and Wilkins, 2000 (specifically part 5: pharmaceutical manufacturing). Suitable excipients are also described in the Handbook of Pharmaceutical Excipients, $2^{nd}$ Edition; Editors A. Wade and P. J. Weller, American Pharmaceutical Association, Washington, The Pharmaceutical Press, London, 1994.

The pharmaceutical compositions of the invention, may be compressed into solid dosage units, such as tablets, or be processed into capsules or suppositories. By means of pharmaceutically suitable liquids the compounds can also be prepared in the form of a solution, suspension, emulsion, or as a spray. For making dosage units, including tablets, the use of conventional additives such as fillers, colorants, polymeric binders and the like is contemplated. In general, any pharmaceutically acceptable additive can be used.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention also provides a pharmaceutical composition of the invention, in combination with packaging material suitable for the composition, the packaging material including instructions for the use of the pharmaceutical composition.

The compositions of the invention are useful in therapy and may be administered to a patient in need thereof. As used herein, the term 'patient' preferably refers to a human patient, but may also refer to a domestic mammal. The term does not encompass laboratory mammals.

In accordance with the sixth aspect of the invention, there is provided a composition as defined according to any one of the first to fourth aspects for use in a method of treating a psychocognitive disorder in a patient. The seventh aspect of the invention provides a method of treating a psychocognitive disorder comprising administering to a patient in need thereof a composition as defined according to any one of the first to fourth aspects and the eighth aspect provides the use of a composition as defined according to any one of the first to fourth aspects in the manufacture of a medicament for use in a method of treating a psychocognitive disorder in a patient.

As used herein the term psychocognitive disorder encompasses psychiatric disorders which may be associated with one or more cognitive impairment. As used herein the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

Diagnostic criteria for psychiatric and psychocognitive disorders referred to herein are provided in the Diagnostic and Statistical Manual of Mental Disorders, Fifth Edition, (DSM-5), the contents of which are incorporated herein by reference.

As used herein the term 'obsessive-compulsive disorder' is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically obsessive-compulsive disorder (OCD) manifests as one or more obsession which drives adoption of a compulsion. For example, an obsession with germs may drive a compulsion to clean. A compulsion can either be overt and observable by others, such as checking that a door is locked, or a covert mental act that cannot be observed, such as repeating a certain phrase in one's mind.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:
  depressed mood, such as feeling sad, empty or tearful (in children and teens, depressed mood can appear as constant irritability);
  significantly reduced interest or feeling no pleasure in all or most activities;
  significant weight loss when not dieting, weight gain, or decrease or increase in appetite (in children, failure to gain weight as expected);
  insomnia or increased desire to sleep;
  either restlessness or slowed behaviour that can be observed by others;
  fatigue or loss of energy;
  feelings of worthlessness, or excessive or inappropriate guilt;
  trouble making decisions, or trouble thinking or concentrating;
  recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:
  A. has depressed mood for most the time almost every day for at least two years. Children and adolescents may have irritable mood, and the time frame is at least one year.
  B. While depressed, a person experiences at least two of the following symptoms:
    Either overeating or lack of appetite.
    Sleeping too much or having difficulty sleeping.
    Fatigue, lack of energy.
    Poor self-esteem.
    Difficulty with concentration or decision making.

As used herein the term 'treatment resistant depression' describes MDD which fails to achieve an adequate response to an adequate treatment with standard of care therapy.

As used herein 'bipolar disorder' also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering a from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein the term 'substance abuse' means a patterned use of a drug in which the user consumes the substance in amounts or with methods which are harmful to themselves or others.

As used herein the term 'an avolition disorder' refers to a disorder which includes as a symptom the decrease in motivation to initiate and perform self-directed purposeful activities.

In preferred embodiments of the sixth to eighth aspects of the present invention, the psychocognitive disorder is selected from (i) an obsessive compulsive disorder, (ii) a depressive disorder, (iii) an anxiety disorder, (iv) substance abuse, and (v) an avolition disorder.

According to particular embodiments of the sixth to eighth aspects of the present invention, the depressive disorder is major depressive disorder. According to still more particular embodiments, the major depressive disorder is treatment-resistant major depressive disorder.

Compositions comprising partially deuterated N,N-dimethyltryptamine compounds of the present invention can be synthesised following the reaction schemes (synthetic schemes) provided in Scheme 1 and Scheme 2 below. The chemistry depicted in the schemes was reported by PE Morris and C Chiao (*Journal of Labelled Compounds And Radiopharmaceuticals*, Vol. XXXIII, No. 6, 455-465 (1993)). Compositions comprising partially deuterated N,N-dimethyltryptamine compounds of the present invention can also be synthesised following the synthetic scheme depicted in Scheme 3 and Example 4 below.

The relative proportions of N,N-dimethyltryptamine against deuterated N,N-dimethyltryptamine compounds and partially deuterated N,N-dimethyltryptamine compounds may be controlled by varying the ratio of lithium aluminium hydride and lithium aluminium deuteride in the reducing agent. Relative proportions may further be varied by adding one or more of N,N-dimethyltryptamine, α,α-dideutero-N,N-dimethyltryptamine and α,α,β,β-tetradeutero-N,N-dimethyltryptamine to the compositions described hereinabove.

A particular advantage of the present invention, in particular but not limited to the compositions obtainable in accordance with its second and third aspects and the method of its ninth aspect, is that the reductions described in accordance with these aspects of the invention allow particularly high purities to be obtained, without the necessity for subsequent chromatographic purification (e.g. column chromatography), thereby increasing the efficiency through which compositions of the invention may be prepared. Moreover, the ability to avoid the use of chromatography in order to achieve high purities makes scale up more efficient and therefore cost-effective.

Identification of the compositions resultant from the reduction step in Schemes 1 and 2 (which represent particular embodiments of the second and third aspects of the invention) may be achieved, if desired, by chromatographic separation of the components of the mixtures by conventional means at the disposal of the skilled person in combination with spectroscopic and/or mass spectrometric analysis.

Scheme 1

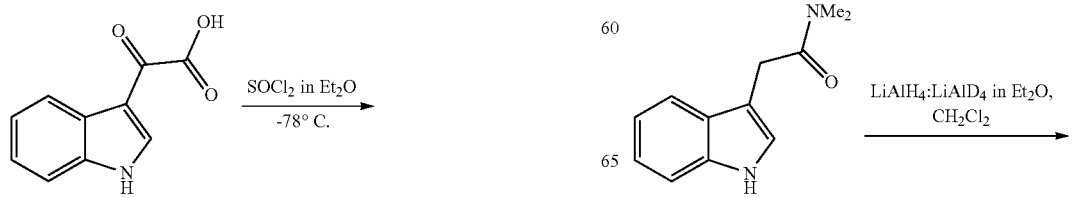

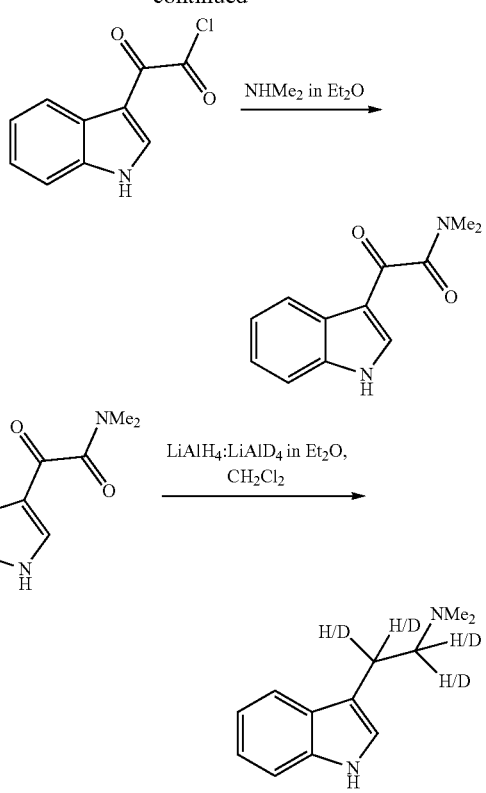

Scheme 2

-continued

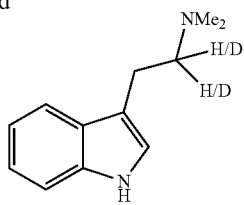

Alternative compositions of the present invention are obtainable by mixing N,N-dimethyltryptamine, obtainable by Scheme 1 or Scheme 2 when the reducing agent is exclusively lithium aluminium hydride, with a deuterated N,N-dimethyltryptamine compound obtainable from Scheme 1 or Scheme 2 when the reducing agent is exclusively lithium aluminium deuteride.

The compositions described hereinabove may be further modified by adding one or more deuterated or partially deuterated N,N-dimethyltryptamine compounds. Stocks of such deuterated or partially deuterated N,N-dimethyltryptamine compounds may be obtained, for example, from the chromatographic separation described above. In this way, for example, the compounds of the tenth aspect of the invention may be obtained. According to particular embodiments of the tenth aspect, the compound is selected from α,β,β-trideutero-N,N-dimethyltryptamine, α,β-dideutero-N,N-dimethyltryptamine, and α-deutero-N,N-dimethyltryptamine.

Whilst identification of the compositions resultant from the reduction described herein may be achieved by chromatographic separation of the components of the mixtures, in combination with spectroscopic and/or mass spectrometric analysis, a particular benefit of the present invention is that, according to particular embodiments, there may be no necessity to do so. This is because, over and above the purities achievable in accordance with the present invention, we have as alluded to above recognised that there is a quantifiable relationship between the extent of deuteration (or in other words the quantity or proportion of deuterium in the N,N-dimethyltryptamine compounds in the compositions of the present invention) and the metabolic half-life of the resultant composition. The extent of deuteration may be controlled through the amount of deuterium-containing reducing agent used in the method of the invention, through which (according to particular embodiments) the compositions of the invention may be obtained, and thus control exercised, in a predictable way, over potentiation of the metabolic half-life of the parent compound (undeuterated N,N-dimethyltryptamine).

Figure 2:
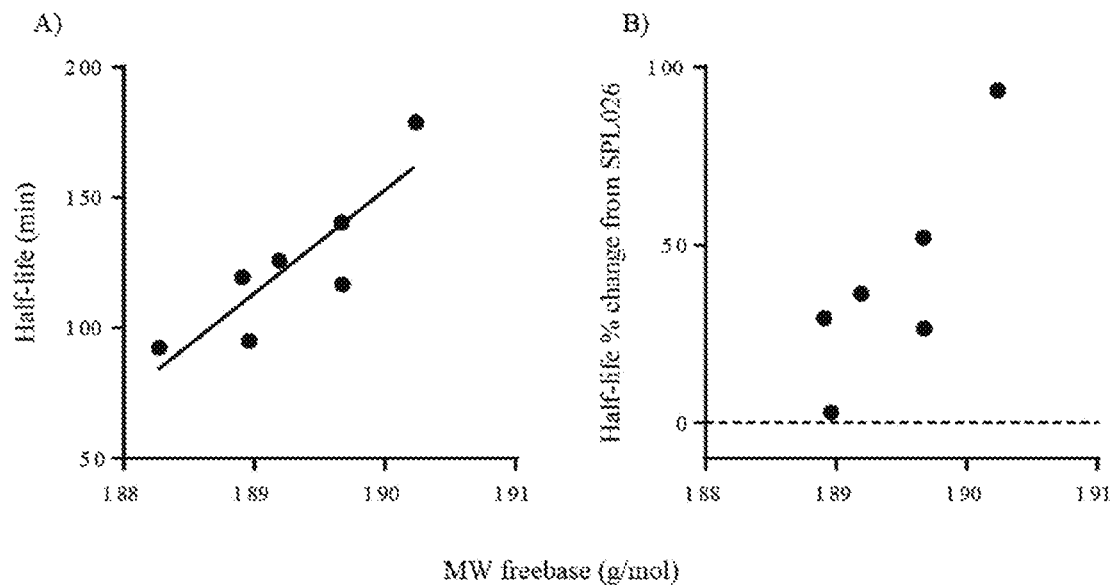
FIG. 2 plots calculated in vitro half-life for DMT and 6 deuterated-containing compositions described in Example 4. A) Linear regression analysis. The r2 value for half-life is 0.754; where the slope was found to be significantly different to zero, p=0.01. B) Half-life of deuterated analogues as a percent change from (undeuterated) DMT (dashed line).
Figure 3:
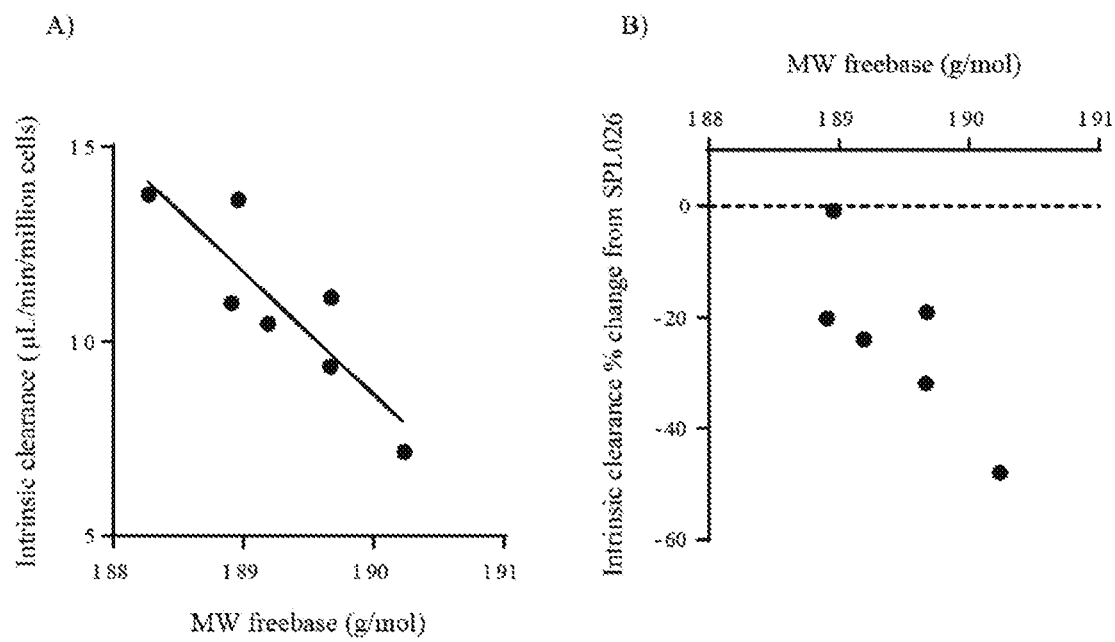
FIG. 3 In vitro intrinsic clearance for DMT and 6 deuterium-containing compositions described in Example 4. A) Linear regression analysis. The $r^2$ value for intrinsic clearance is 0.7648; where the slope was found to be significantly different to zero, p=0.01. B) Intrinsic clearance of deuterated analogues as a percent change from (undeuterated) DMT (dashed line).

In particular, as detailed in Example 4 and related FIGS. 2 and 3, we have demonstrated that increasing deuterium enrichment at the α-carbon of N,N-dimethyltryptamine increases metabolic stability, leading to a decrease in clearance and longer half-life. A linear relationship exists between molecular weight and half-life, in particular when the input reducing agent for production of the deuterium-enriched N,N-dimethyltryptamine-containing compositions of this invention comprise $LiAlH_4$ and $LiAlD_4$ with ratio between about 1:2.5 and about 2.5:1.

Such types of composition constitute specific embodiments of the first aspect of the invention. According to these specific embodiments, the composition consists essentially of a mixture of N,N-dimethyltryptamine and one or both of α-deutero-N,N-dimethyltryptamine and α,α-dideutero-N,N-dimethyltryptamine, the composition optionally being in the form of a pharmaceutically acceptable salt, wherein the mean molecular weight of N,N-dimethyltryptamine, α-deutero-N,N-dimethyltryptamine and α,α-dideutero-N,N-dimethyltryptamine present in the composition is from 188.28 to 190.28.

As used herein, mean molecular weight means the weighted average of molecular weights of the of the N,N-dimethyltryptamine and one or both of α-deutero-N,N-dimethyltryptamine and α,α-dideutero-N,N-dimethyltryptamine, as measured by an appropriate mass spectroscopic technique, for example LC-MS SIM (selected-ion monitoring), ignoring any weight contribution by formation of pharmaceutically acceptable salts, where applicable.

It will be understood that providing compositions with such specific mean molecular weights can be achieved by those skilled in the art through the teachings herein, in particular by adjusting the relative proportions of lithium aluminium hydride and lithium aluminium deuteride in the reductions described herein.

In this context, by reciting that the composition consists essentially of the mixture of N,N-dimethyltryptamine and one or both of α-deutero-N,N-dimethyltryptamine and α,α-dideutero-N,N-dimethyltryptamine means that the composition may comprise additional components to these but that the presence of such additional components will not materially affect the essential characteristics of the composition. In particular, the composition will not comprise material quantities of other pharmaceutically active compounds, including other N,N-dimethyltryptamine compounds. Thus material quantities of other deuterated N,N-dimethyltryptamine compounds, in particular β-deutero-N,N-dimethyltryptamine compounds and β,β-dideutero-N,N-dimethyltryptamine compounds, such as β-deutero-N,N-dimethyltryptamine and β,β-dideutero-N,N-dimethyltryptamine and β-deutero-N,N-dimethyltryptamine compounds and β,β-dideutero-N,N-dimethyltryptamine compounds having respectively one or two deuterium atoms in place of hydrogen atoms at the α position not present in compositions of such embodiments.

In other words, and alternatively put, the compositions according to these specific embodiments constitute a drug substance comprising a biologically active ingredient consisting essentially of a mixture of N,N-dimethyltryptamine and one or more of α-deutero-N,N-dimethyltryptamine and α,α-dideutero-N,N-dimethyltryptamine, wherein the biologically active ingredient has a mean molecular weight from 188.28 to 190.28 and wherein the drug substance is optionally in the form of a pharmaceutically acceptable salt.

It will be understood that the compositions according to these specific embodiments comprise one or more of α-deutero-N,N-dimethyltryptamine and α,α-dideutero-N,N-dimethyltryptamine in amounts greater than found in isotopically unenriched N-dimethyltryptamine. It will also be understood that the greater the proportion of α-deutero-N,N-dimethyltryptamine and α,α-dideutero-N, N-dimethyltryptamine in these specific embodiments, the higher the mean molecular weight of the composition.

According to more specific embodiments, the mean molecular weight of N,N-dimethyltryptamine, α-deutero-N,N-dimethyltryptamine and α,α-dideutero-N,N-dimethyltryptamine present in the composition is from 188.9 to 189.7, for example 188.90 to 189.70.

According to still more specific embodiments of the specific embodiments described herein, including compositions in which the mean molecular weight of N,N-dimethyltryptamine, α-deutero-N,N-dimethyltryptamine and α,α-dideutero-N,N-dimethyltryptamine present in the composition is from 188.9 to 189.7, for example 188.90 to 189.70, the composition optionally is in the form of a pharmaceutically acceptable salt, by which it will be understood that the N,N-dimethyltryptamine, α-deutero-N,N-dimethyltryptamine and α,α-dideutero-N,N-dimethyltryptamine present in the composition are present in pharmaceutically acceptable salt form. Such salts may be as described elsewhere herein and, according to yet more specific embodiments, the composition is in the form of a fumarate salt.

Each and every patent and non-patent reference referred to herein is hereby incorporated by reference in its entirety, as if the entire contents of each reference were set forth herein in its entirety.

The invention may be further understood with reference to the following non-limiting clauses and examples following thereafter:

1. A composition comprising two or more compounds selected from N,N-dimethyltryptamine, deuterated N,N-dimethyltryptamine, and partially deuterated N,N-dimethyltryptamine.
2. The composition of clause 1 comprising a combination of N,N-dimethyltryptamine and 2% or more by weight of one or more deuterated or partially deuterated N,N-dimethyltryptamine compound, wherein a deuterated N,N-dimethyltryptamine compound is substituted with two deuterium atoms at the α position and a partially deuterated N,N-dimethyltryptamine compound is an N,N-dimethyltryptamine compound with one hydrogen atom and one deuterium atom at the α position.
3. The composition of clause 1 or 2 wherein the deuterated N,N-dimethyltryptamine compound is selected from α,α-dideutero-N,N-dimethyltryptamine and α,α,β,β-tetradeutero-N,N-dimethyltryptamine.
4. The composition of clause 3 comprising 2% or more by weight of α,α,β,β-tetradeutero-N,N-dimethyltryptamine.
5. The composition of clause 3 or 4 comprising 2% or more by weight of α,α-dideutero-N,N-dimethyltryptamine.
6. The composition of any one of clauses 1 to 5 comprising one or more partially deuterated N,N-dimethyltryptamine compound selected from α,β,β-trideutero-N,N-dimethyltryptamine, α,β-dideutero-N,N-dimethyltryptamine, and α-deutero-N,N-dimethyltryptamine.
7. The composition of clause 6 wherein the partially deuterated N,N-dimethyltryptamine compound is α-deutero-N,N-dimethyltryptamine.
8. The composition of any one of clauses 1 to 7 wherein the one or more partially deuterated N,N-dimethyltryptamine compound comprises up to 50% by weight of the total composition.
9. The composition of any one of clauses 1 to 8 comprising from 5% to 95% by weight of N,N-dimethyltryptamine.
10. The composition of any one of clauses 1 to 9 comprising from 5% to 95% by weight of a deuterated N,N-dimethyltryptamine compound selected from α,α-dideutero-N,N-dimethyltryptarnine and α,α,β,β-tetradeutero-N,N-dimethyltryptamine.
11. A composition obtainable by the reduction of 2-(3-indolyl)-N,N-dimethylglyoxalamide with a reducing agent consisting essentially of up to 90% by weight of lithium aluminium hydride and 10% or more of lithium aluminium deuteride.
12. A composition obtainable by the reduction of 2-(3-indolyl)-N, N-dimethylacetamide with a reducing agent consisting essentially of up to 90% by weight of lithium aluminium hydride and 10% or more of lithium aluminium deuteride.
13. The composition of any one of clauses 1 to 12 for use in treating a psychiatric or psychocognitive disorder in a patient.
14. The composition for use according to clause 13 wherein the psychiatric or psychocognitive disorder is selected from (i) an obsessive compulsive disorder, (ii) a depressive disorder, (iii) an anxiety disorder, (iv) substance abuse, and (v) an avolition disorder.
15. A compound selected from α,β,β,β-trideutero-N,N-dimethyltryptamine, α,β-dideutero-N,N-dimethyltryptamine, and α-deutero-N,N-dimethyltryptamine.

EXAMPLES

Example 1

2-(3-indolyl)-N,N-dimethylacetamide is synthesised as described in Morris and Chiao (1993), Journal of labelled compounds and radiopharmaceuticals, Vol. XXXIII, No. 6. 0.063 g $LiAlH_4$ and 0.278 g $LiAlD_4$ (20:80 molar ratio of $LiAlH_4$:$LiAlD_4$) are suspended in 25 ml dry $Et_2O$ with magnetic stirring. 0.785 g of 2-(3-indolyl)-N,N-dimethylacetamide is dissolved in 300 mL and added dropwise to the stirred suspension. The reagents are heated under reflux for 3 hours, then cooled in an ice bath and quenched dropwise with water. The resulting mixture is filtered, dried, and the solvents removed under vacuum, to yield approx. 0.5 g of a composition consisting of 3 molar % N,N-dimethyltryptamine, 28 molar % α-deutero-N,N-dimethyltryptamine and 69 molar % of α,α-dideutero-N,N-dimethyltryptamine.

Example 2

0.173 g $LiAlH_4$ and 0.156 g $LiAlD_4$ (55:45 molar ratio of $LiAlH_4$:$LiAlD_4$) are suspended in 25 ml dry $Et_2O$ with magnetic stirring. 0.785 g of 2-(3-indolyl)-N,N-dimethylacetamide is dissolved in 300 mL and added dropwise to the stirred suspension. The reagents are heated under reflux for 3 hours, then cooled in an ice bath and quenched dropwise with water. The resulting mixture is filtered, dried, and the solvents removed under vacuum, to yield approx. 0.5 g of a composition consisting of 24 molar % N,N-dimethyltryptamine, 50 molar % α-deutero-N,N-dimethyltryptamine and 26 molar % of α,α-dideutero-N,N-dimethyltryptamine.

Example 3

0.293 g $LiAlH_4$ and 0.035 g $LiAlD_4$ (90:10 molar ratio of $LiAlH_4$:$LiAlD_4$) are suspended in 25 ml dry $Et_2O$ with magnetic stirring. 0.785 g of 2-(3-indolyl)-N,N-dimethylacetamide is dissolved in 300 mL and added dropwise to the stirred suspension. The reagents are heated under reflux for 3 hours, then cooled in an ice bath and quenched dropwise with water. The resulting mixture is filtered, dried, and the solvents removed under vacuum, to yield approx. 0.5 g of a composition consisting of 76 molar % N,N-dimethyltryptamine, 22 molar % α-deutero-N,N-dimethyltryptamine and 2 molar % of α,α-dideutero-N,N-dimethyltryptamine.

Example 4: Use of Human Hepatocytes to Assess the In Vitro Intrinsic Clearance of Deuterated DMT Analogue Blends Relative to DMT In vitro determination of intrinsic clearance is a valuable model for predicting in vivo hepatic clearance. The liver is the main organ of drug metabolism in the body, containing both phase I and phase II drug metabolising enzymes, which are present in the intact cell.

Synthesis of Samples

N,N-DMT 220.9 g (as free base) was prepared as N,N-DMT fumarate, using the chemistry depicted in Scheme 3. An additional 4-6 g of six partially deuterated mixtures were also produced using modified conditions.

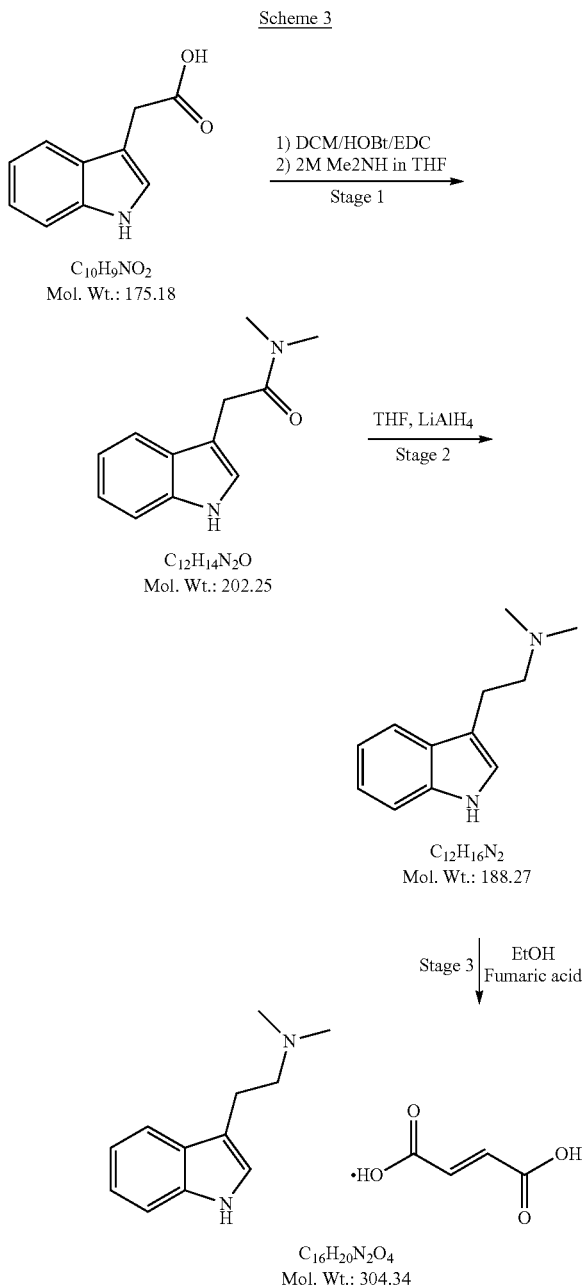

Scheme 3

Synthesis of DMT

Stage 1: Coupling of Indole-3-Acetic Acid and Dimethylamine

To a 5 L vessel under $N_2$ was charged indole-3-acetic acid (257.0 g, 1.467 mol), hydroxybenzotriazole (HOBt, ~20% wet) (297.3 g, 1.760 mol) and dichloromethane (2313 mL) to give a milky white suspension. 1-Ethyl-3-(3-dimethylaminopropyl) carbodiimide hydrochloride (EDC.HCl, 337.5 g, 1.760 mol) was then charged portion-wise over 5 minutes at 16-22° C. The reaction mixture was stirred for 2 hours at ambient temperature before 2M dimethylamine in THF (1100 mL, 2.200 mol) was charged dropwise over 20 minutes at 20-30° C. The resultant solution was stirred at ambient temperature for 1 hour where HPLC indicated 1.1% indole-3-acetic acid and 98.1% target product referred to as Stage 1). The reaction mixture was then charged with 10% $K_2CO_3$ (1285 mL) and stirred for 5 minutes. The layers were separated, and the upper aqueous layer extracted with dichloromethane (643 mL×2). The organic extracts were combined and washed with saturated brine (643 mL). The organic extracts were then dried over $MgSO_4$, filtered and concentrated in vacuo at 45° C. This provided 303.1 g of crude Stage 1 as an off-white sticky solid. The crude material was then subjected to a slurry in tert-butyl methyl ether (TBME, 2570 mL) at 50° C. for 2 hours before being cooled to ambient temperature, filtered and washed with TBME (514 mL×2). The filter-cake was then dried in vacuo at 50° C. to afford Stage 1 266.2 g (yield=90%) as an off-white solid in a purity of 98.5% by HPLC and >95% by NMR.

Stage 2: Preparation of DMT

To a 5 L vessel under $N_2$ was charged Stage 1 (272.5 g, 1.347 mol) and tetrahydrofuran (THF, 1363 mL) to give an off-white suspension. 2.4 M $LiAlH_4$ in THF (505.3 mL, 1.213 mol) was then charged dropwise over 35 minutes at 20-56° C. to give an amber solution. The solution was heated to 60° C. for 2 hours where HPLC indicated Stage 1 ND, target product bracket referred to as Stage 2, 92.5%), Impurity 1 (2.6%), Impurity 2 (1.9%). The complete reaction mixture was cooled to ambient temperature and then charged to a solution of 25% Rochelle's salts (aq) (2725 mL) dropwise over 30 minutes at 20-30° C. The resultant milky white suspension was allowed to stir at 20-25° C. for 1 hour after which the layers were separated and the upper organic layer washed with saturated brine (681 mL). The organic layer was then dried over $MgSO_4$, filtered and concentrated in vacuo at 45° C. The resultant crude oil was subjected to an azeotrope from ethanol (545 mL×2). This provided 234.6 g (yield=92%) of Stage 2 in a purity of 95.0% by HPLC and >95% by NMR.

Stage 3a (i)-(iii): Preparation of Seed Crystals of DMT Fumarate (i) Stage 2 (100 mg) was taken up in 8 volumes of isopropyl acetate and warmed to 50° C. before charging fumaric acid (1 equivalent) as a solution in ethanol. The flask was then allowed to mature at 50° C. for 1 hour before cooling to room temperature and stirring overnight, resulting in a white suspension. The solids were isolated by filtration and dried for 4 hours at 50° C. to provide 161 mg of product (>99% yield). Purity by HPLC was determined to be 99.5% and by NMR to be >95%.

(ii) Substitution of isopropyl acetate for isopropyl alcohol in method (i) afforded a white suspension after stirring overnight. The solids were isolated by filtration and dried for 4 hours at 50° C. to provide 168 mg of product (>99% yield). Purity by HPLC was determined to be 99.8% and by NMR to be >95%.

Substitution of isopropyl acetate for tetrahydrofuran in method (i) afforded a white suspension after stirring overnight. The solids were isolated by filtration and dried for 4 hours at 50° C. to provide 161 mg of product (>99% yield). Purity by HPLC was determined to be 99.4% and by NMR to be >95%.

Analysis by x-ray powder diffraction, showed the products of each of methods 9i) to (iii) to be the same, which was labelled Pattern A.

Stage 3b: Preparation of DMT Fumarate

To a 5 L flange flask under $N_2$ was charged fumaric acid (152.7 g, 1.315 mol) and Stage 2 (248.2 g, 1.315 mol) as a solution in ethanol (2928 mL). The mixture was heated to 75° C. to give a dark brown solution. The solution was polish filtered into a preheated (80° C.) 5 L jacketed vessel. The solution was then cooled to 70° C. and seeded with Pattern A (0.1 wt %), the seed was allowed to mature for 30 minutes before cooling to 0° C. at a rate of 5° C./hour. After stirring for an additional 4 hours at 0° C., the batch was filtered and washed with cold ethanol (496 mL×2) and then dried at 50° C. overnight. This provided 312.4 g (yield=78%) of Stage 3 in a purity of 99.9% by HPLC and >95% by NMR. XRPD: Pattern A Synthesis of Deuterated Mixtures of DMT Compounds A modified synthesis at stage 2 using solid $LiAlH_4$/$LiAlD_4$ mixtures was adopted, using 1.8 equivalents of $LiAlH_4$/$LiAlD_4$ versus 0.9 equivalents using the process described above for undeuterated DMT.

Six deuteration reactions were performed.

Representative Synthesis of a Deuterated Mixture (Using 1:1 $LiAlH_4$:$LiAlD_4$) of DMT Compounds To a 250 mL 3-neck flask under $N_2$ was charged $LiAlH_4$ (1.013 g, 26.7 mmol), $LiAlD_4$ (1.120 g, 26.7 mmol) and THF (100 mL). The resultant suspension was stirred for 30 minutes before stage 1 (6 g, 29.666 mmol) was charged portion-wise over 15 minutes at 20-40° C. The reaction mixture was then heated to reflux (66° C.) for 2 hours where HPLC indicated no stage 1 remained. The mixture was cooled to 0° C. and quenched with 25% Rochelle's salts (aq) (120 mL) over 30 minutes at <30° C. The resultant milky suspension was stirred for 1 hour and then allowed to separate. The lower aqueous layer was removed and the upper organic layer washed with saturated brine (30 mL). The organics were then dried over $MgSO_4$, filtered and concentrated in vacuo. This provided 4.3 g of crude material.

The crude was then taken up in ethanol (52 mL) and charged with fumaric acid (2.66 g, 22.917 mmol) before heating to 75° C. The resultant solution was allowed to cool to ambient temperature overnight before further cooling to 0-5° C. for 1 hour. The solids were isolated by filtration and washed with cold ethanol (6.5 mL×2). The filtercake was dried at 50° C. overnight to provided 5.7 g (yield=63%) of product in a purity of 99.9% by HPLC and >95% by NMR.

Assessment of Extents of Deuteration

This was achieved by LCMS-SIM (SIM=single ion monitoring), the analysis giving a separate ion count for each mass for the three deuterated N,N-dimethyltryptamine compounds (N,N-dimethyltryptamine (D0), α-deutero-N,N-dimethyltryptamine (D1) and α,α-dideutero-N,N-dimethyltryptamine (D2)) at the retention time for N,N-dimethyltryptamine. The percentage of each component was then calculated from these ion counts.

For example, % D0=[D0/(D0+D1+D2)]×100.

HPLC Parameters

| System: | Agilent 1100/1200 series liquid chromatograph or equivalent |
| --- | --- |
| Column: | Triart Phenyl; 150 × 4.6 mm, 3.0 μm particle size (Ex: YMC, Part number: TPH12S03-1546PTH) |
| Mobile phase A: | Water:Trifluoroacetic acid (100:0.05%) |
| Mobile phase B: | Acetonitrile:Trifluoroacetic acid (100:0.05%) |

| Gradient: | Time | % A | % B |
| --- | --- | --- | --- |
| | 0 | 95 | 5 |
| | 13 | 62 | 38 |
| | 26 | 5 | 95 |
| | 30.5 | 5 | 95 |
| | 31 | 95 | 5 |

| Flow rate: | 1.0 mL/min | | |
| --- | --- | --- | --- |
| Stop time: | 31 minutes | Post runtime: | 4 minutes |
| Injection volume: | 5 μL | Wash vial: | N/A |
| Column temperature: | 30° C. combined | | |
| Wavelength: | 200 nm, (4 nm) | Reference: | N/A |

Mass Spectrometry Parameters

| System: | Agilent 6100 series Quadrupole LC-MS or equivalent | | |
| --- | --- | --- | --- |
| Drying gas flow: | 12.0 L/min | Drying gas temp.: | 350° C. |
| Nebuliser pressure: | 35 psig | Gain: | 1.00 |
| Fragmentor: | 110 | | |

| Cpd | RT | RRT | Conc | Diluent | Detection | Mass |
| --- | --- | --- | --- | --- | --- | --- |
| D0 | 10.64 | 1.00 | 0.30 mg/ml | $CH_3CN$:$H_2O$ (50:50) | (+) SIM | 189.10 m/z |
| D1 | 10.64 | 1.00 | 0.30 mg/ml | $CH_3CN$:$H_2O$ (50:50) | (+) SIM | 190.10 m/z |
| D2 | 10.64 | 1.00 | 0.30 mg/ml | $CH_3CN$:$H_2O$ (50:50) | (+) SIM | 191.10 m/z |

MS-SIM range is the target mass ±0.1 m/z

The data for the six deuterated reactions are tabulated in Table 1 below:

| Mixture No. (LiAlH₄:LiAlD₄ ratio) | Input (stage 1) | Output stage 3 (yield) | Purity by HPLC | Purity by NMR | Deuteration % | | |
|---|---|---|---|---|---|---|---|
| | | | | | $D_0$ | $D_1$ | $D_2$ |
| 1 (SPL026) (0:1) | 5 g | 5.3 g (65%) | 99.7% | >95% | 0.7% | 2.7% | 96.6% |
| 2 (1:1) | 6 g | 5.699 g (63%) | 99.9% | >95% | 30.0% | 48.3% | 21.7% |
| 3 (1:2) | 5 g | 4.206 g (52%) | 99.9% | >95% | 16.5% | 46.8% | 36.8% |
| 4 (1:3) | 5 g | 5.558 g (68% | 99.8% | >95% | 9.3% | 41.5% | 49.2% |
| 5 (2:1) | 5 g | 4.218 g (52%) | 99.9% | >95% | 47.5% | 41.3% | 11.2% |
| 6 (3:1) | 5 g | 5.0 g (62%) | 99.4% | >95% | 57.5% | 35.3% | 7.4% |

In Vitro Intrinsic Clearance of DMT (SPL026) and 6 Deuterated Compound Blends

In vitro determination of intrinsic clearance is a valuable model for predicting in vivo hepatic clearance. The liver is the main organ of drug metabolism in the body, containing both phase I and phase II drug metabolising enzymes, which are present in the intact cell.

Aim

To use human hepatocytes to assess the in vitro intrinsic clearance of deuterated DMT analogue blends relative to DMT.

Description of the Experiment

Human (mixed gender) hepatocytes pooled from 10 donors (0.545 million cells/mL) were used to investigate the in vitro intrinsic clearance of DMT and 6 deuterated analogues.

A concentration of 5 µM was used for all test compounds, as well as sumatriptan, serotonin, benzylamine controls. This concentration was chosen in order to maximise the signal-to-noise ratio, while remaining under the Michaelis constant (Km) for the monoamine oxidase enzyme (MAO). Diltiazem and diclofenac controls were used at a laboratory-validated concentration of 1 µM.

Test compounds were mixed with the hepatocyte suspension within a 96-well plate and incubated for up to 60 minutes at 37° C. The suspension was continuously agitated. At 7 time points, small aliquots were withdrawn, and the test compound/blend concentration therein was measured by LC-MS/MS. The time points measured were 2, 4, 8, 15, 30, 45 and 60 minutes.

The following LC-MS/MS conditions were used for the analysis:
Instrument: Thermo TSQ Quantiva with Thermo Vanquish UPLC system
Column: Luna Omega 2.1×50 mm 2.6 µm
Solvent A: H₂O+0.1% formic acid
Solvent B: Acetonitrile+0.1% formic acid
Flow rate: 0.8 ml/min
Injection vol: 1 µl
Column temp: 65° C.
Gradient:

| Time (mins) | % Solvent B |
|---|---|
| 0.00 | 5.0 |
| 0.90 | 75.0 |
| 1.36 | 99.0 |
| 1.36 | 5.0 |
| 1.80 | 5.0 |

Ms Parameters:

Positive ion spray voltage: 4000 V

Vaporiser temperature: 450° C.

Ion transfer tube temp: 365° C.

Sheath gas: 54

Aux gas: 17

Sweep gas: 1

Dwell time 8 ms

MRM transitions:

D0=mass to charge ratio 189.14>58.16.

D1=mass to charge ratio 190.14>59.17.

D2=mass to charge ratio 191.14>60.17.

The MRM transitions were determined from a preliminary analysis of DMT samples containing either no deuterium (for D0 transition), or high levels of either D1 or D2 deuteration (for the D1 and D2 transitions respectively).

The resulting concentration-time profile was then used to calculate intrinsic clearance (CLint) and half-life (t½). To do this, the MS peak area or MS peak area/IS response of each analyte is plotted on a natural log scale on the y axis versus time (min) of sampling on the X axis. The slope of this line is the elimination rate constant. This is converted to a half-life by −ln(2)/slope. Intrinsic clearance is calculated from the slope/elimination rate constant and the formula is CLint=(−1000*slope)/cell density in 1E6 cells/ml, to give units of microlitre/min/million cells.

Results

Intrinsic clearance and half-life values were calculated for DMT and the 6 deuterated mixtures described above. These data were weighted dependent on the ratio of D0, D1 and D2 to give an overall intrinsic clearance and half-life value for each compound blend (Table 2).

TABLE 2

In vitro intrinsic clearance and calculated half-life of DMT and 6 deuterated mixtures

| Compound name or Mixture No (per Table 1) | LiAlH$_4$:LiAlD$_4$ input ratio | D$_0$:D$_1$:D$_2$ output ratio | Molecular weight | Intrinsic clearance (μL/min/ million cells) | Half-life (min) |
|---|---|---|---|---|---|
| DMT (SPL026) | 1:0 | 100:0:0 | 188.269 | 13.77 | 92.39 |
| 1 | 0:1 | 0.7:2.7:96.6 | 190.240 | 7.15 | 178.79 |
| 2 | 1:1 | 30.0:48.3:21.7 | 189.192 | 10.46 | 125.80 |
| 3 | 1:2 | 16.5:46.8:36.8 | 189.669 | 9.36 | 140.43 |
| 4 | 1:3 | 9.3:41.5:49.2 | 189.676 | 11.14 | 116.84 |
| 5 | 2:1 | 47.5:41.3:11.2 | 188.910 | 10.99 | 119.61 |
| 6 | 3:1 | 57.4:35.3:7.4 | 188.961 | 13.64 | 95.04 |

Data were fitted with a linear model using regression analysis, which revealed that deuterium enrichment at the α-carbon of DMT decreases intrinsic clearance linearly with increasing molecular weight (MW), therefore enabling manufacture of DMT drug substances with half-lives which can be accurately predicted in the range identified.

Mixture 1, which contains 96.6% D2-DMT, sees the biggest change, with the intrinsic clearance rate almost halved compared to undeuterated-DMT (FIG. 3), nearly doubling the half-life (FIG. 2). Intermediate blends of deuteration (Mixtures 2 to 5) decreased intrinsic clearance in a manner correlated with molecular weight (FIG. 3).

CONCLUSION

These data demonstrate that increasing deuterium enrichment at the α-carbon of DMT increases metabolic stability, leading to a decrease in clearance and longer half-life. A linear relationship exists between MW and half-life, in particular when the input reducing agent for production of the deuterium enriched DMT-containing drug substance by methods of the present invention comprise LiAlH$_4$ and LiAlD$_4$ with ratio between 1:2.5 and 2.5:1.

The invention claimed is:

1. A deuterium-enriched N,N-dimethyltryptamine mixture consisting essentially of:

N,N-dimethyltryptamine, including pharmaceutically acceptable salts thereof; and 50% or more by weight in total of α-protio, α-deutero-N,N-dimethyltryptamine of the formula

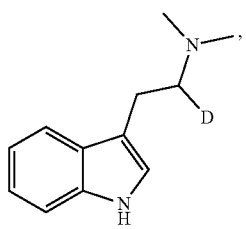

including pharmaceutically acceptable salts thereof; and
α,α-dideutero-N,N-dimethyltryptamine of the formula

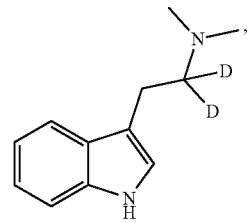 [SMILES: [2H]C([2H])(Cc1c[nH]c2ccccc12)N(C)C]

including pharmaceutically acceptable salts thereof;
wherein the mixture comprises 2% or more by weight of the α-protio, α-deutero-N,N-dimethyltryptamine, including pharmaceutically acceptable salts thereof; and
wherein the deuterium-enriched N,N-dimethyltryptamine mixture has a purity of greater than or equal to 99% by HPLC.

2. The deuterium-enriched N,N-dimethyltryptamine mixture of claim 1, wherein the mixture comprises 2% or more by weight of the α,α-dideutero-N,N-dimethyltryptamine or a pharmaceutically acceptable salt thereof.

3. The deuterium-enriched N,N-dimethyltryptamine mixture of claim 1, wherein the mixture comprises from 10% to 98% by weight of the α,α-dideutero-N,N-dimethyltryptamine, including pharmaceutically acceptable salts thereof.

4. The deuterium-enriched N,N-dimethyltryptamine mixture of claim 1, wherein the mixture comprises up to 50% by weight of the α-protio, α-deutero-N,N-dimethyltryptamine, including pharmaceutically acceptable salts thereof.

5. The deuterium-enriched N,N-dimethyltryptamine mixture of claim 1, wherein the pharmaceutically acceptable salt is a fumarate salt.

6. The deuterium-enriched N,N-dimethyltryptamine mixture of claim 1, wherein the mixture comprises between 2% and 50% by weight of the α-protio, α-deutero-N,N-dimethyltryptamine, including pharmaceutically acceptable salts thereof.

7. The deuterium-enriched N,N-dimethyltryptamine mixture of claim 1, wherein the mixture has a purity of greater than or equal to 99.9% by HPLC.

8. The deuterium-enriched N,N-dimethyltryptamine mixture of claim 1, wherein the mixture comprises 60% or more by weight in total of the α-protio, α-deutero-N,N-dimethyltryptamine and the α,α-dideutero-N,N-dimethyltryptamine, including pharmaceutically acceptable salts thereof.

9. The deuterium-enriched N,N-dimethyltryptamine mixture of claim 1, wherein the mixture comprises 75% or more by weight in total of the α-protio, α-deutero-N,N-dimethyltryptamine and the α,α-dideutero-N,N-dimethyltryptamine, including pharmaceutically acceptable salts thereof.

* * * * *